(12) United States Patent
Marbet

(10) Patent No.: US 11,612,687 B2
(45) Date of Patent: Mar. 28, 2023

(54) DRUG DELIVERY DEVICE

(71) Applicant: SENSILE MEDICAL AG, Olten (CH)

(72) Inventor: Regina Marbet, Rütschelen (CH)

(73) Assignee: SENSILE MEDICAL AG, Olten (CH)

( * ) Notice: Subject to any disclaimer, the term of this patent is extended or adjusted under 35 U.S.C. 154(b) by 741 days.

(21) Appl. No.: 16/348,515

(22) PCT Filed: Nov. 7, 2017

(86) PCT No.: PCT/EP2017/078470
§ 371 (c)(1),
(2) Date: May 9, 2019

(87) PCT Pub. No.: WO2018/087089
PCT Pub. Date: May 17, 2018

(65) Prior Publication Data
US 2019/0358393 A1    Nov. 28, 2019

(30) Foreign Application Priority Data

Nov. 10, 2016 (EP) ..................................... 16198070

(51) Int. Cl.
*A61M 5/14* (2006.01)
*A61M 5/142* (2006.01)
(Continued)

(52) U.S. Cl.
CPC .......... *A61M 5/14248* (2013.01); *A61J 1/201* (2015.05); *A61J 1/2003* (2015.05);
(Continued)

(58) Field of Classification Search
CPC .............. A61M 5/14248; A61M 5/158; A61M 5/14244; A61M 5/14566;
(Continued)

(56) References Cited

U.S. PATENT DOCUMENTS 8,070,739 B2 * 12/2011 Zinger .................. A61J 1/2096
604/411
2003/0036725 A1 * 2/2003 Lavi .................... A61M 5/2066
604/91
(Continued)

FOREIGN PATENT DOCUMENTS

WO    WO 02/24259      3/2002
WO    WO 2015/177652   11/2015

OTHER PUBLICATIONS

Written Opinion in International Application No. PCT/EP2017/078470, dated Feb. 8, 2018, pp. 1-7.

Primary Examiner — Nathan R Price
Assistant Examiner — Tania Ismail
(74) Attorney, Agent, or Firm — Saliwanchik, Lloyd & Eisenschenk

(57) ABSTRACT

A drug delivery device comprising a delivery unit (2) including an internal reservoir (8), a subcutaneous delivery mechanism (6), a pump for pumping liquid from the internal reservoir to the subcutaneous delivery system, and a liquid filling mechanism (12) configured for injecting liquid from an external vial (16) or reservoir into the internal reservoir. The liquid filling mechanism comprises a filling port (14) and a valve mechanism (18) selectively operable to: open a first fluid path (54) extending from the filling port to the internal fluid reservoir and close a second fluid path (56) extending from the internal reservoir to the subcutaneous delivery member, or close the first fluid path and open the second fluid path. The valve mechanism comprises a valve housing (48) fixedly mounted in relation to a housing of the drug delivery device and a valve stem (50) rotatably received within the valve housing, whereby the first fluid path and the second fluid path are selectively operated by the rotational position of the valve stem in relation to the valve housing, such that when the valve stem is in a first position, (Continued)

the first fluid path is open while the second fluid path is closed, and when the valve stem is in a second position, the second fluid path is open while the first fluid path is closed.

15 Claims, 10 Drawing Sheets

(51) Int. Cl.
A61M 39/22 (2006.01)
A61M 5/315 (2006.01)
A61M 5/145 (2006.01)
A61M 5/158 (2006.01)
A61M 5/31 (2006.01)
A61M 5/20 (2006.01)
A61J 1/20 (2006.01)
A61M 5/178 (2006.01)

(52) U.S. Cl.
CPC ............ A61J 1/2006 (2015.05); A61J 1/2037 (2015.05); A61J 1/2096 (2013.01); A61M 5/14244 (2013.01); A61M 5/14566 (2013.01); A61M 5/158 (2013.01); A61M 5/1782 (2013.01); A61M 5/204 (2013.01); A61M 39/223 (2013.01); A61M 2005/14252 (2013.01); A61M 2005/14268 (2013.01); A61M 2005/1585 (2013.01); A61M 2005/3114 (2013.01); A61M 2005/31588 (2013.01); A61M 2039/226 (2013.01); A61M 2039/229 (2013.01); A61M 2205/502 (2013.01); A61M 2209/045 (2013.01)

(58) Field of Classification Search
CPC ........... A61M 2005/1585; A61M 2005/14268; A61M 2005/14252; A61M 2005/31588; A61M 2209/045; A61M 39/223; A61M 2039/226; A61M 2039/229; A61M 5/1782; A61M 5/204; A61M 2005/3114; A61J 1/2003; A61J 1/2006; A61J 1/201; A61J 1/2037; A61J 1/2096
See application file for complete search history.

(56) References Cited

U.S. PATENT DOCUMENTS

2013/0296807 A1* 11/2013 Lintern .................... A61J 1/20
604/272
2019/0328960 A1* 10/2019 Gravesen ................ F16L 29/02

* cited by examiner

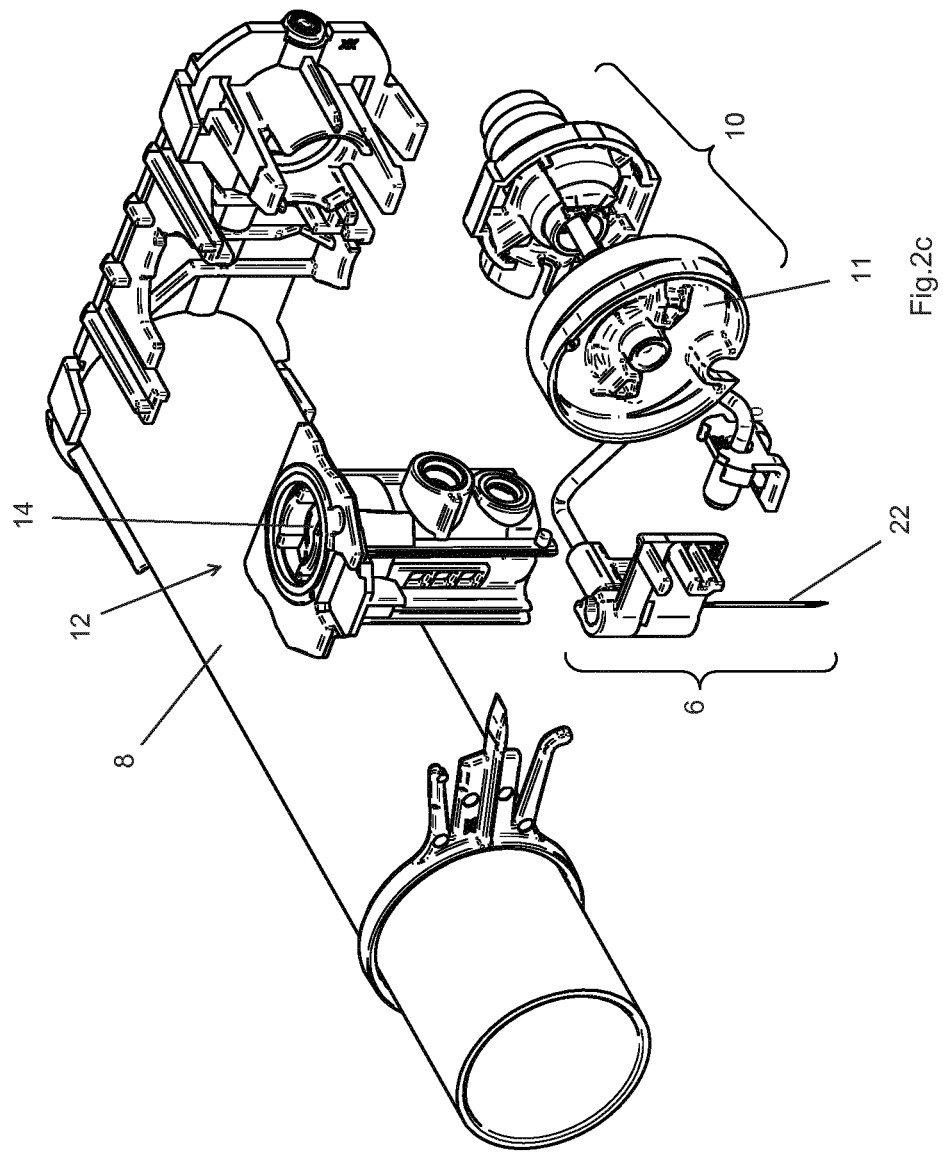

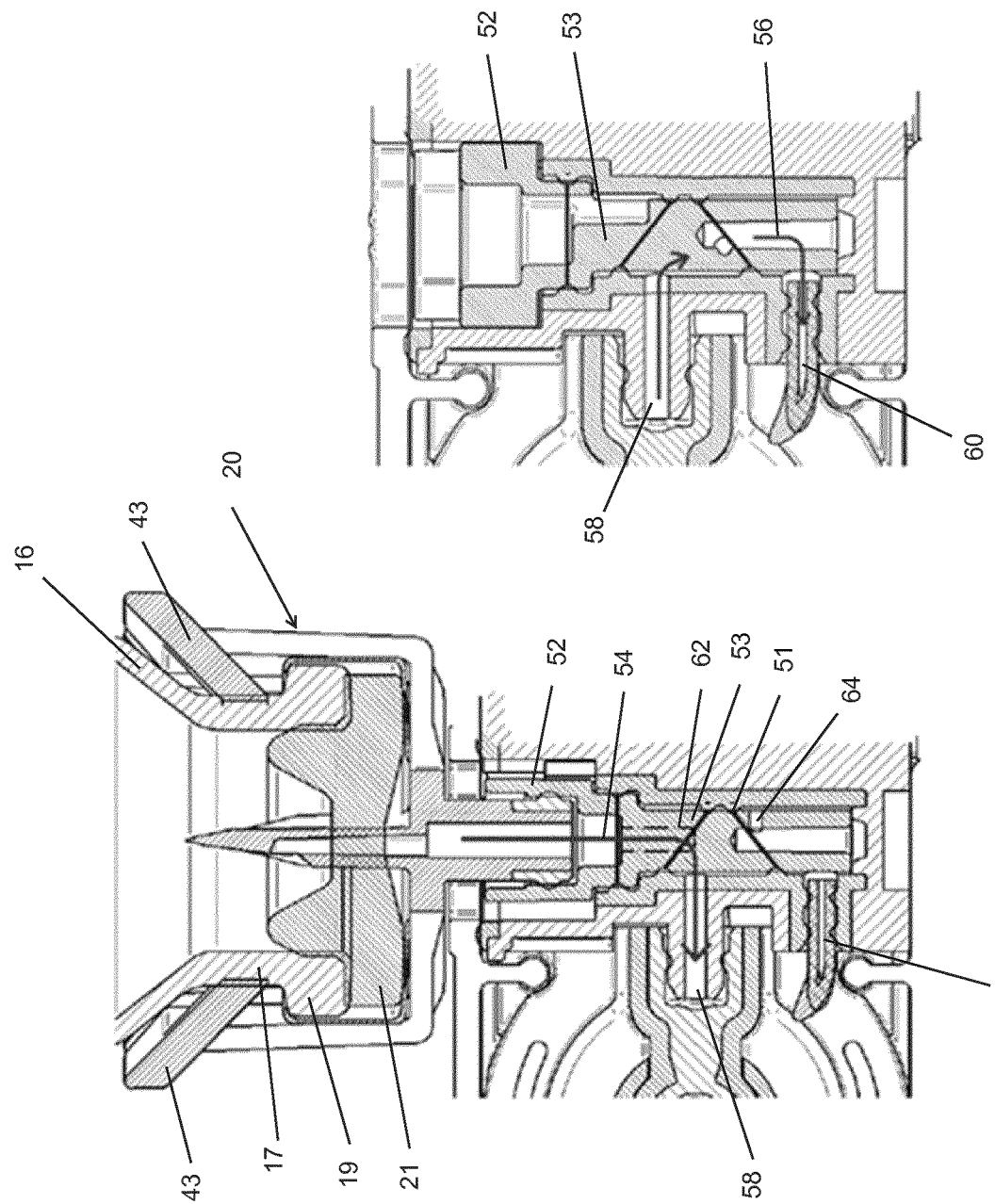

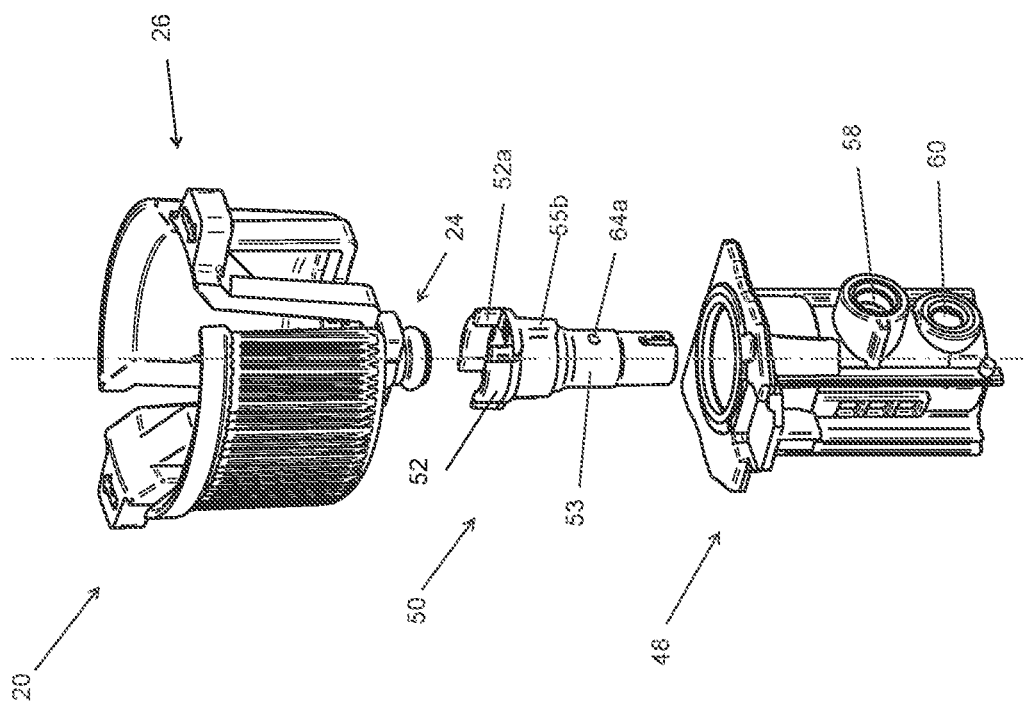

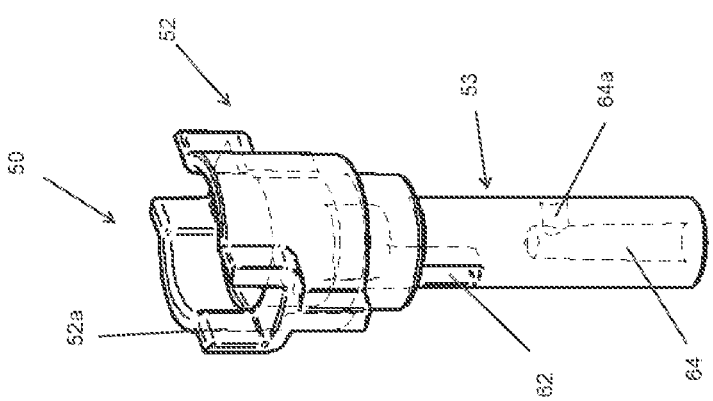
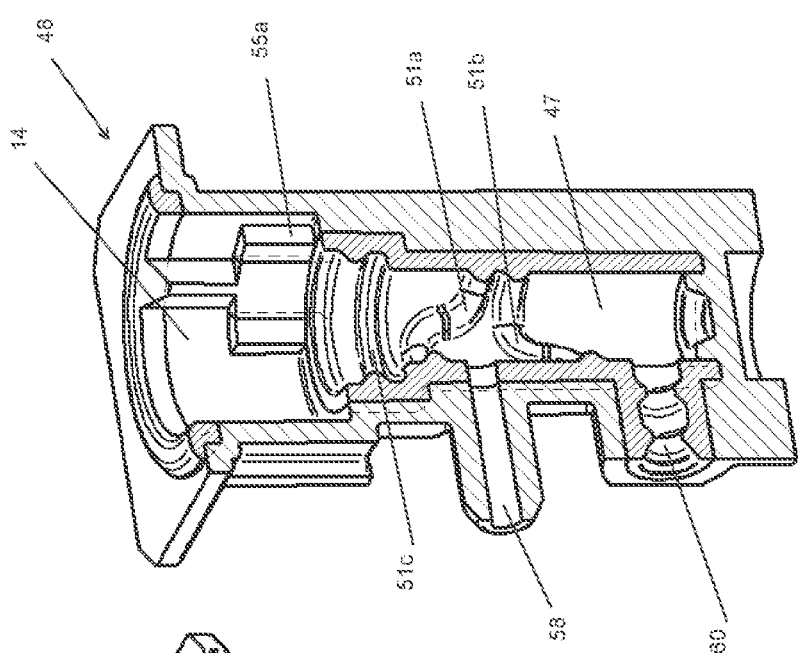
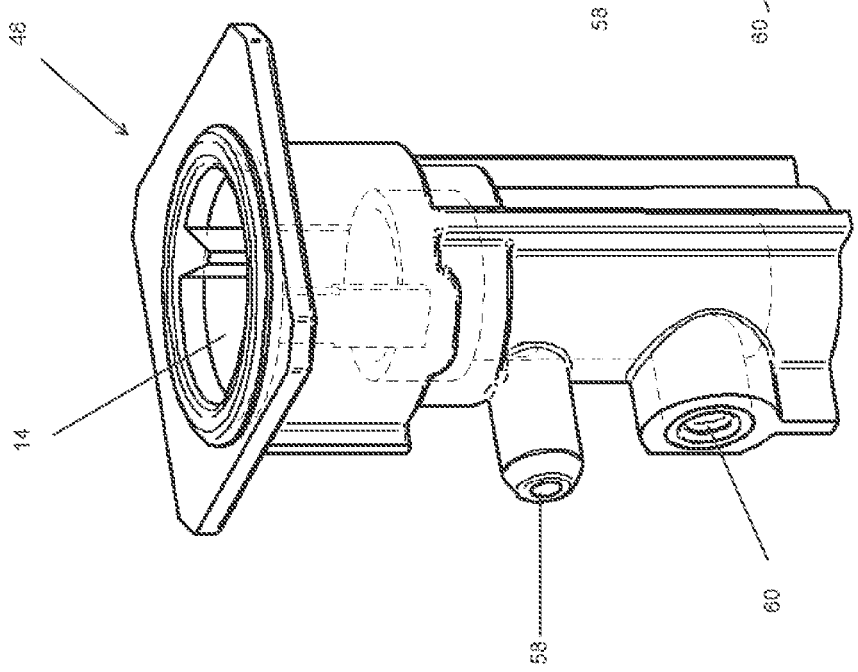

DRUG DELIVERY DEVICE

CROSS-REFERENCE TO RELATED APPLICATION

This application is the U.S. national stage application of International Patent Application No. PCT/EP2017/078470, filed Nov. 7, 2017.

TECHNICAL FIELD

The present invention relates to a drug delivery device, suitable for subcutaneously delivering a medicament.

DESCRIPTION OF RELATED ART

Regular trans-dermal administration of doses of a medicament is necessary in the control or therapy of many conditions, such as diabetes, growth hormone deficiency, pain therapy, and chemotherapy. For instance, diabetic patients may require injections of insulin several times a-day. The insulin dosage regime required for a diabetic patient varies depending on a number of factors including, for instance, the type of diabetes, the type of insulin administered, the actual severity of the condition, the lifestyle of the patient, the routine and diet of the patient. Accordingly, diabetic patients often need to administer doses of insulin themselves, several times perday, and in places other than hospitals or medical centres.

A number of drug delivery devices have been developed to facilitate the self-administration of medicaments. Such devices may for instance comprise needle actuation mechanisms which can be operated to cause a needle to be automatically inserted into a user. The drug delivery devices are typically provided with an internal reservoir containing a liquid medicament and when the internal reservoir is empty, the drug delivery device is opened and the reservoir is replaced.

An example of a drug delivery device connectable with a vial adapter is disclosed in US 2013/0296807. A vial is mechanically coupled to a connector such that rotation of the vial causes the adapter and vial to rotate in unison. Rotation of the vial in either a first or a second direction causes the vial to be either locked or unlocked to/from the adapter. Specifically, by rotating the vial adapter, a cartridge conduit is either fluidly connected or disconnected to an injection conduit for delivery of a medicament to a patient. The reservoirs in the fluid supply circuits are connected by needles and sealed off with membranes, into which needles are penetrated and retracted.

However, the drug delivery device in US 2013/0296807 involves a plurality of internal needles and septums in order to establish and switch between a delivery fluid path and a refill fluid path. Septums that are pierced several times risk of getting worn out with a tendency for leakage.

SUMMARY OF THE INVENTION

An object of the invention is to provide a drug delivery device with an internal fluid reservoir that may be filled with a liquid supplied externally prior to first use of the device, or after first use of the device for refilling thereof. The drug delivery device should be safe and easy to use, in particular should not require complex manipulations by the user.

It would be advantageous to provide a drug delivery device which is easy to fill or refill and reduces the risk of leakage and contamination of the fluid medicament during filling.

It would be advantageous to provide a drug delivery device which is compact and economical to produce.

It would be advantageous, for certain medical applications, to provide a wearable drug delivery device.

Objects of the invention are achieved by a drug delivery device according to claim 1.

Disclosed herein is a drug delivery device comprising a delivery unit including an internal reservoir, a subcutaneous delivery mechanism, a pump for pumping liquid from the internal reservoir to the subcutaneous delivery system, and a liquid filling mechanism configured for injecting liquid from an external reservoir or vial into the internal reservoir, the liquid filling mechanism comprising a filling port and a valve mechanism selectively operable to:

open a first fluid path extending from the filling port to the internal fluid reservoir and close a second fluid path extending from the internal reservoir to the subcutaneous delivery member, or close the first fluid path and open the second fluid path, wherein the valve mechanism comprising a valve housing fixedly mounted in relation to a housing of the drug delivery device and a valve stem rotatably received within the valve housing, whereby the first fluid path and the second fluid path are selectively operated by the rotational position of the valve stem in relation to the valve housing, such that when the valve stem is in a first position, the first fluid path is open while the second fluid path is closed, and when the valve stem is in a second position, the second fluid path is open while the first fluid path is closed.

Advantageously, since the internal reservoir can be filled by an external vial, the user is not required to open the device and replace components in order to fill or refill the internal reservoir. Additionally, the fluid paths within the valve are easily operated by rotating the external vial from a first insertion position to a locked second position, that turns the valve stem in relation to the valve housing.

In an embodiment, the valve housing comprises a cavity comprising a sealing portion in which a valve stem portion of the valve stem is lodged. The valve stem portion comprises a first valve stem channel and a second valve stem channel. The valve housing comprises a first fluid channel fluidically connected to the internal reservoir and a second fluid channel fluidically connected to the subcutaneous delivery mechanism. The sealing portion further comprises a first angular seal positioned between the filling port and the first fluid channel, but before the second fluid channel, and a second angular seal positioned between the first fluid channel and the second fluid channel, whereby when the first angular seal is bridged by the first valve stem channel, fluid communication between the filling port and the first fluid channel is established, and when the second angular seal is bridged by said second valve stem channel, fluid communication between the first fluid channel and second fluid channel is established.

The drug delivery may comprise a reusable base unit and a disposable delivery unit, wherein the delivery unit houses the pump and the liquid filling mechanism.

The liquid filling mechanism of the present drug delivery device may further comprise a vial adapter which is configured to interconnect a vial to the filling port of the drug delivery device. The vial adapter and liquid filling mechanism may comprise mating male-female connecting members, such that the vial adapter can be locked to the filling port upon an axial insertion followed by a rotation in relation to the housing, or by a spiral movement of simultaneous axial and rotational displacement, whereby in the locked position the first fluid path is opened and the second fluid path is closed, and when the vial adapter is in an unlocked position or removed from the filling port, the second fluid path is opened and the first fluid path is closed.

In an embodiment, the filling port may comprise a keyed aperture configured to receive axially therethrough a keyed member of the vial adapter, the keyed member comprising at least one flange or locking shoulder engaging a complementary locking member of the keyed aperture to hold the vial adapter to the fluid delivery device.

The keyed member may comprise two or more radial protrusions extending transversely from the axial direction of the vial adapter.

The valve stem may comprise a coupling portion arranged at a top end of a valve stem portion, the coupling portion being accessible through the filling port and configured to engage with the complementary keyed member of the vial adapter for driving rotation of the valve stem between the first position and the second position.

The coupling portion of the valve stem may be configured as a female connector, configured to engage with a male keyed member provided on the vial adapter.

In an embodiment, the first fluid channel and the second fluid channel of the valve stem connect to a lateral surface of the valve stem and are spaced apart at an angular distance of between 90° and 180°.

In an exemplary embodiment, the same pump is used for pumping fluid to the subcutaneous delivery mechanism and for pumping fluid to the internal fluid reservoir.

In an exemplary embodiment, the rotational position of the valve stem governs the direction of rotation of the pump.

The vial adapter may further comprise a position indicator cooperating with a position indicator on the liquid filling mechanism for guiding the user to turn the vial adapter to a required angle in which the valve stem is in the second position.

The vial adapter may comprise a first connecting portion configured such that the vial adapter can be fixedly connected to the filling port, and a second connecting portion configured such that the vial adapter can be fixedly connected to an external vial, the vial adapter further comprising a channel which extends from the first connecting portion to the second connecting portion in order to transfer fluid from the vial into the valve mechanism, the first connecting portion comprising an extension configured to be inserted into the filling port and couple to a coupling portion of the valve stem, a seal being provided on the extension or an internal circumference of the valve housing such that the extension is sealed against the internal circumference of the valve housing. In an embodiment, the second connecting portion is provided with a piercing member adapted to penetrate a septum, membrane or a cover of a vial. The second connecting portion may also comprise a snap fit locking arm configured to lock the vial adapter to a neck of the vial.

Further objects and advantageous features of the invention will be apparent from the claims, from the detailed description, and annexed drawings, in which:

BRIEF DESCRIPTION OF THE DRAWINGS

FIG. 2c is an exploded perspective view of the delivery unit of FIG. 2a;

FIGS. 3a and 3b are cross sectional views of a portion of a drug delivery device according to an embodiment of the invention, FIG. 3a showing the liquid filling mechanism of the device connected to an external vial for filling of an internal reservoir of the drug delivery device (valve mechanism in a first position) and FIG. 3b showing the device after filling with the external vial removed (valve mechanism in a second position);

FIG. 5 is an exploded perspective view of a liquid filling mechanism of a drug delivery unit according to an embodiment of the invention;

FIGS. 6a and 6b are perspective and cross-sectional views of a valve housing of the mechanism of FIG. 5;

FIG. 7 is a perspective view of a valve stem of the mechanism of FIG. 5;

DETAILED DESCRIPTION OF EXEMPLARY EMBODIMENTS

Figure 1A:
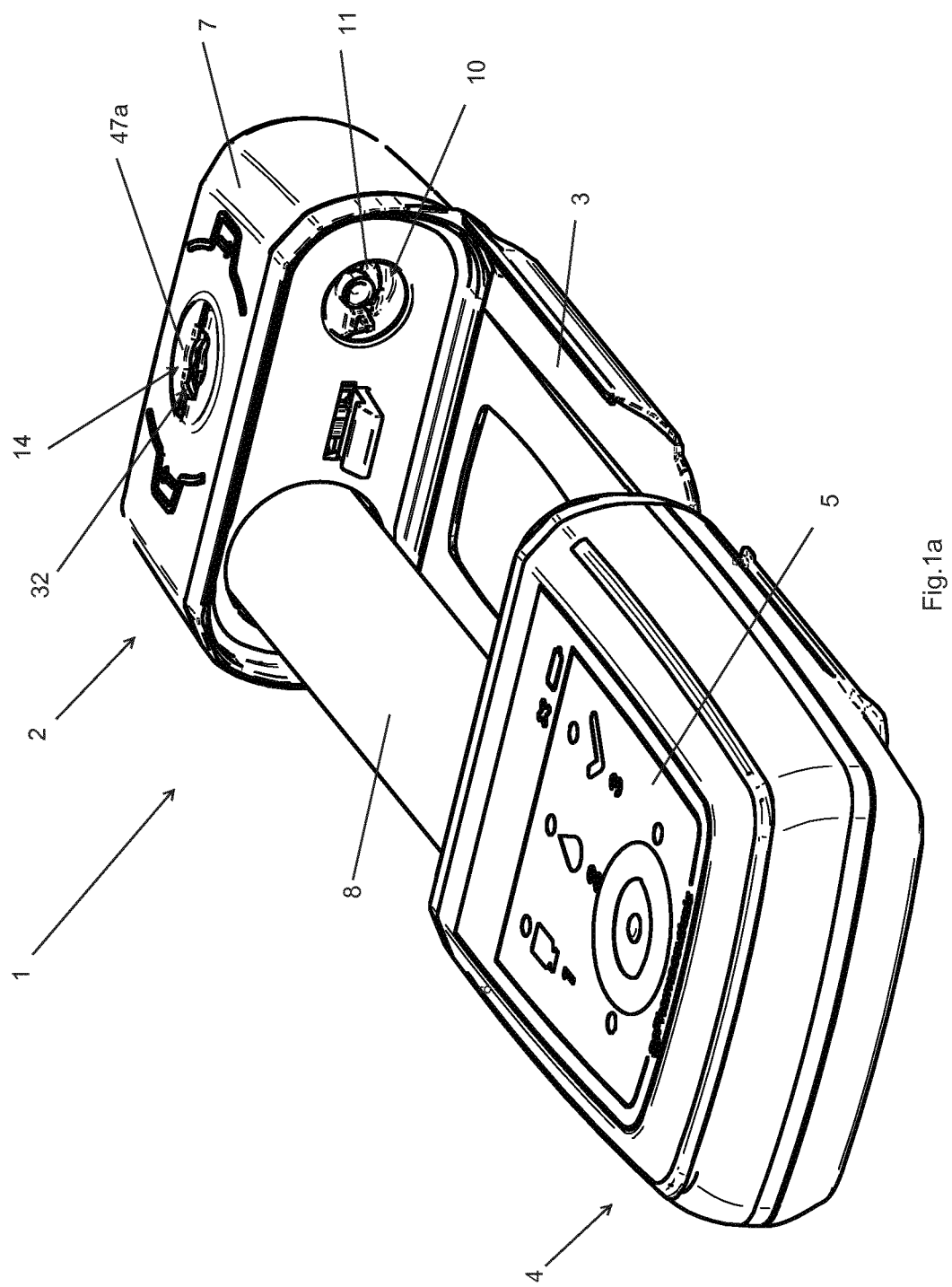
FIG. 1a is a view in perspective of a drug delivery device comprising a base unit and a delivery unit in a disassembled state, according to an embodiment of the invention.
Figure 1C:
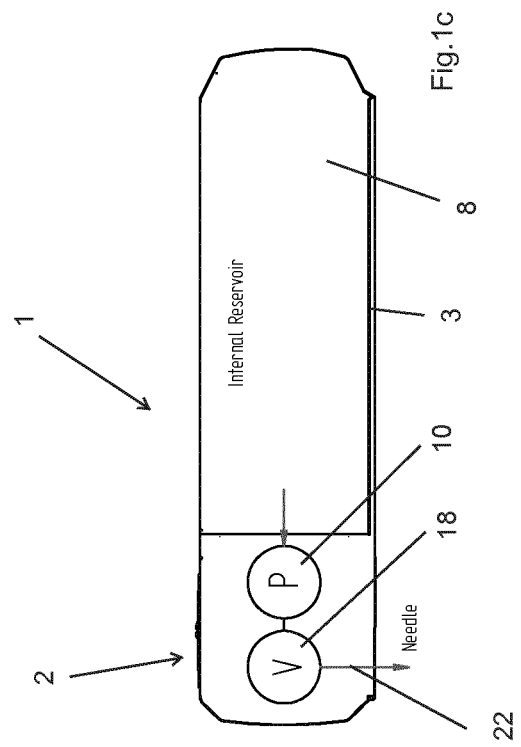
FIGS. 1b and 1c are a simplified schematic cross sectional views of a drug delivery device according to an embodiment of the invention, FIG. 1b showing the device connected to an external vial for filling of an internal reservoir of the drug delivery device and FIG. 1c showing the device after filling.
Figure 1B:
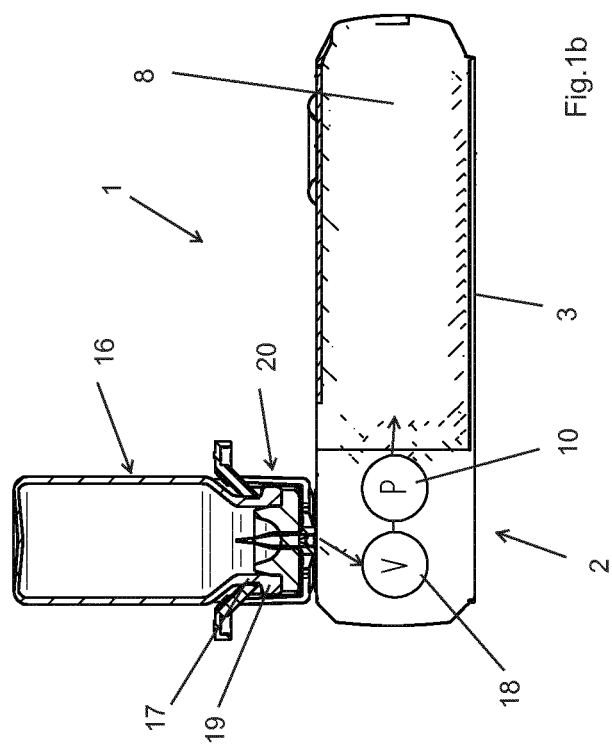
Figure 2A:
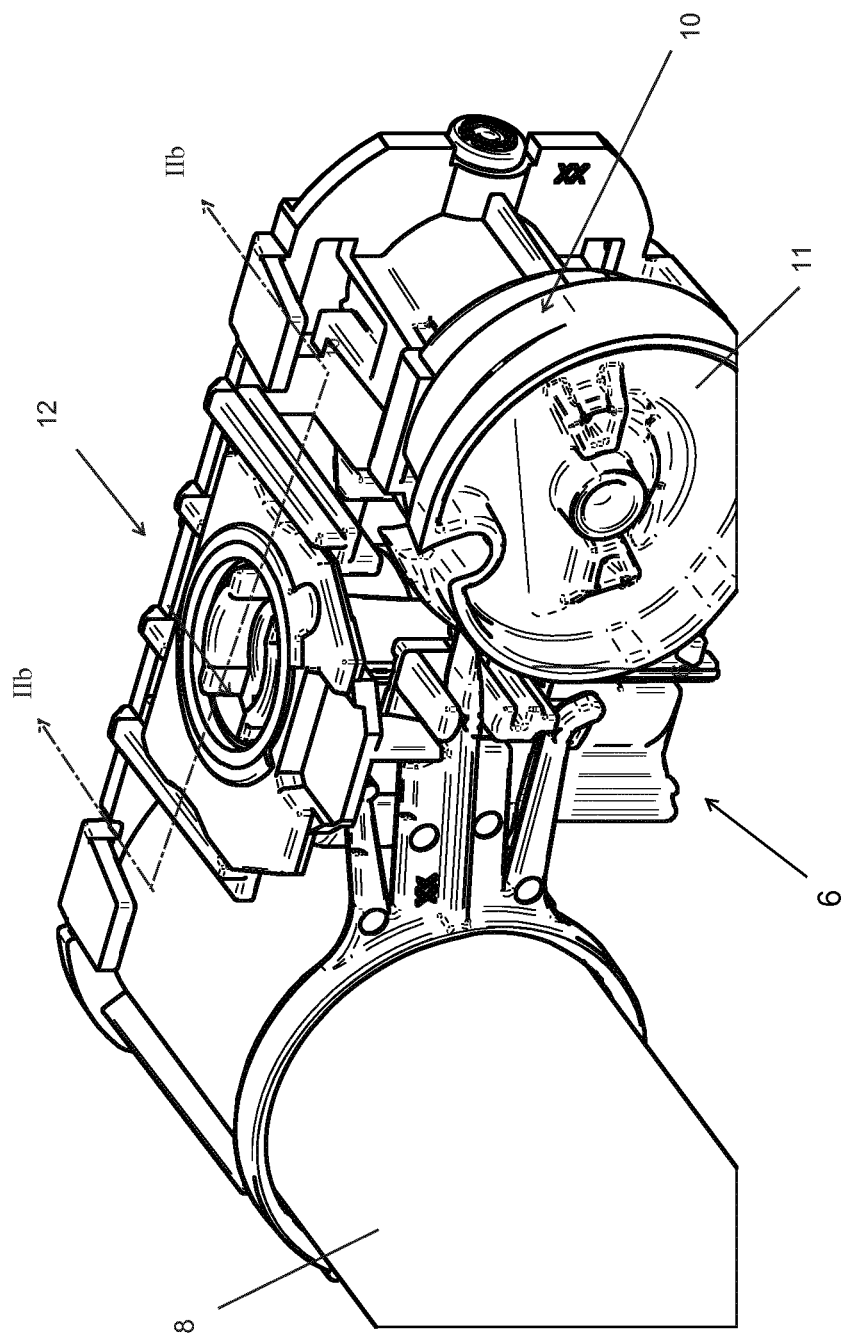
FIG. 2a is a view in perspective of the delivery unit of FIG. 1a, shown without housing.
Figure 2B:
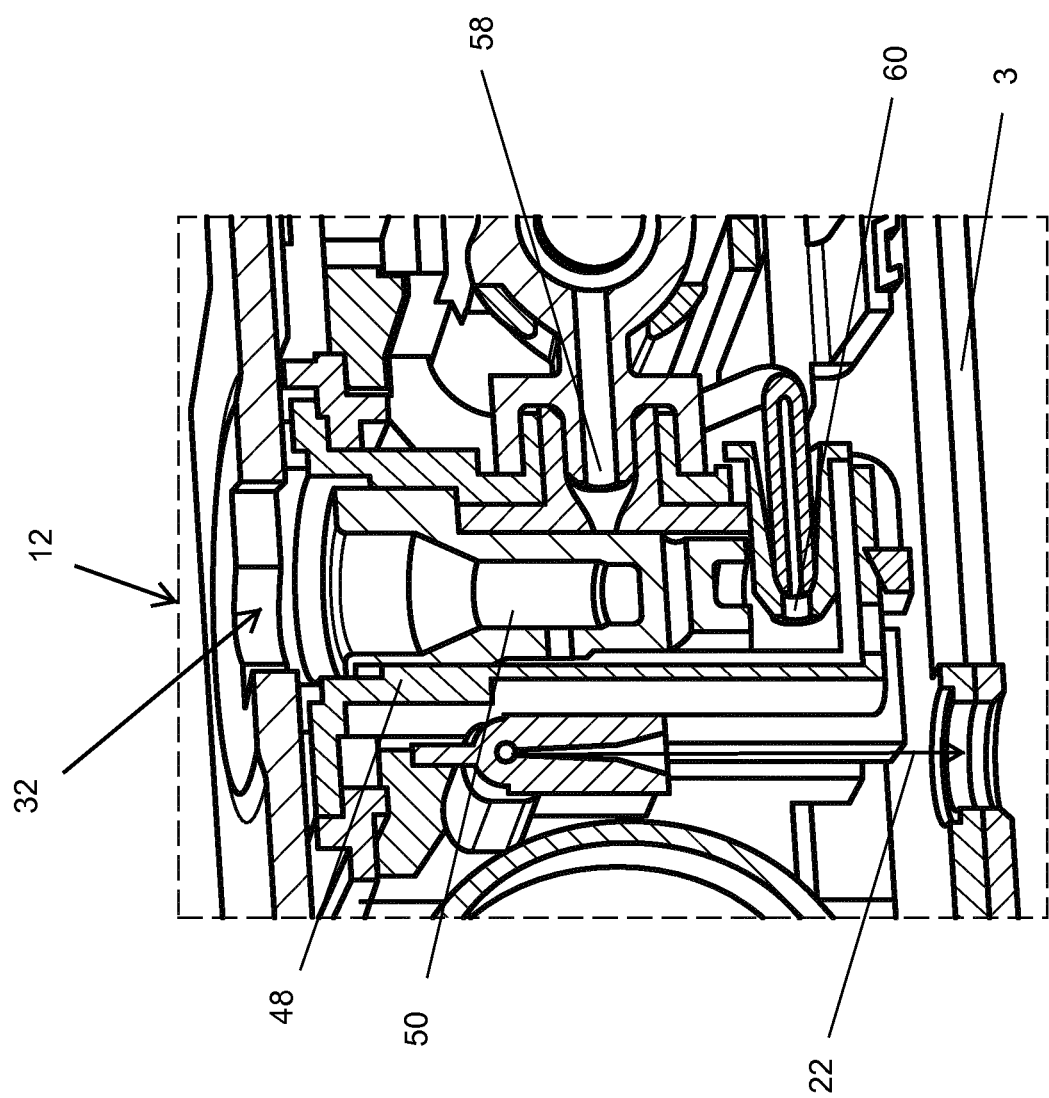
FIG. 2b is a cross-sectional view through line of FIG. 2a, but shown with the housing.

As best seen in FIGS. 1a to 1c, a drug delivery device 1 of the present invention comprises a delivery unit 2 and a base unit 4. In this illustrated embodiment the delivery unit 2 is removably connected to the base unit 4, although it will be appreciated that in other embodiments they may be formed integrally. The delivery unit 2 comprises a housing 7 and housed therein a subcutaneous delivery mechanism 6 for delivering a liquid drug transdermally. A liquid drug is stored, prior to administration to the patient, in an internal reservoir 8 forming part of the delivery unit 2. The delivery unit 2 further comprises a pump 10 mounted in the housing 7, the pump being configured to transfer the liquid from the internal reservoir 8 to the subcutaneous delivery mechanism 6. In an advantageous embodiment, the subcutaneous delivery mechanism comprises a delivery needle 22 mounted within the housing 7 in a retracted state (as best seen in FIG. 2b) prior to first use, the delivery needle being actuated into an extended state projecting beyond the base 3 of the device for drug administration. The needle 22 may also be used to insert a supple cannula (not shown) through the patient's skin and then retract such that the cannula forms the liquid path for transdermal delivery of liquid drug to the patient. Such delivery mechanisms are per se known and shall not be further described herein. Other embodiments are also possible within the scope of this invention, for instance the fluid delivery unit may be connected to a catheter configured for delivering liquid drugs to the patient via the catheter at a location remote from the drug delivery device.

The base unit 4 comprises a housing, a pump drive configured to drive the pump of the delivery unit 2, a battery or other form of power source, and an electronic control unit for controlling the liquid administration to the patient and other operations of the drug delivery device. The control unit may include a user interface 5 comprising for instance a display and command buttons for user control or access to information.

The pump 10 mounted in the delivery unit may advantageously comprise a drive coupling interface 11 configured to be engaged by a complementary coupling interface of a pump drive mounted in the base unit 4. The pump in the illustrated embodiment is a rotary pump comprising a rotor mounted in a stator (such rotary pumps being per se known), the drive coupling interface 11 coupled to a rotor of the pump and therefore also being configured to rotate. The pump drive mounted in the base unit in this example may thus comprise a rotary motor where the rotor is coupled directly or via a reduction gear mechanism to the complementary drive coupling interface.

In an embodiment, the delivery unit may be a disposable unit and the base unit may be a reusable unit. The drug delivery device 1 may advantageously be provided in the form of a patch device whereby the disposable delivery unit 2 comprises an adhesive base 3 for mounting against a patient's skin.

In use, the drug delivery device 1 is configured to deliver liquid from the internal reservoir 8 to the patient, via the subcutaneous delivery mechanism 6. In an embodiment, after a certain number of doses have been delivered, the drug delivery device 1 may be refilled with liquid while the internal reservoir 8 is left inside the drug delivery device 1.

In certain embodiments, the internal reservoir 8 may be supplied with a drug constituent in a dry form stored in the internal reservoir 8, for instance a lyophilized powder form. The internal reservoir 8 may then be filled shortly prior to first use with another drug constituent in the form of a liquid, for instance a liquid solvent or liquid excipient, to prepare the medication for administration to the patient. The reconstitution of drugs provided as two constituents, in particular a solid constituent and a liquid constituent, is per se well known and allows to store drugs for longer periods as the dry solid form is generally less sensitive to alteration.

The delivery unit 2 includes a liquid filling mechanism 12 comprising a filling port 14 and a valve mechanism 18, such that the internal reservoir 8 of the drug delivery device 1 can be filled or refilled with liquid from an external liquid container 16 such as a vial 16. Typically, vials 16 containing drugs in a liquid form, or solvents or excipients as mentioned previously, are provided in the shape of sealed bottles. The shape and sizes of the vials may be standard or widely used, or may be custom or special shapes and sizes, depending on the application.

Many standard vials 16 for medications, as best illustrated in FIGS. 1b and 3a, have a reduced diameter neck 17 with a rim 19 at the outlet end of the vial, a septum 21 or cap hermetically closing the outlet orifice at the outlet end.

As schematically illustrated in the embodiment of FIGS. 1b and 3a, the liquid filling mechanism 12 may further comprise a vial adapter 20 configured to couple the outlet end of the vial 16 to the filling port 14 of the drug delivery device 1. Alternatively, the vial 16 may comprise an outlet end with an integrated connection member (not shown) configured to directly engage and couple with the filling port 14 of the drug delivery device 1.

As illustrated in FIGS. 1b and 3a, the internal reservoir 8 may be filled with liquid stored in an external vial 16 by bringing the vial 16 into a fluid communication with the internal reservoir 8 through the filling port 14 and valve mechanism 18. Specifically, the valve mechanism 18 can be selectively operated to either allow a liquid transfer from the vial 16 via the filling port 14 to the internal reservoir 8, or to allow a fluid transfer from the internal reservoir 8 to the delivery needle 22. Preferably, a single common pump 10 can be used for performing both the filling operation and the drug delivery. However, other solutions are possible within the scope of the invention. For instance, a dual pump configuration is possible, with one pump for the filling operation and a separate second pump for drug delivery. Yet another solution is to have a pump for the drug delivery mounted within the housing 7, whereas the filling operation is performed using an external pressure source not forming part of the delivery unit. The external pressure source may for instance include an external pump or a plunger coupled to the external vial or container, operated for instance by the user, or a liquid provided under pressure within the external container.

In an exemplary embodiment of the present invention as illustrated in FIGS. 2b to 7, the valve mechanism 18 comprises a valve housing 48 which is fixedly received within the housing 7 of the delivery unit 2, and a rotatable valve stem 50 received within a cavity 47 of the valve housing 48. The valve stem 50 has a vial coupling portion 52 and a valve stem portion 53, the vial coupling portion 52 disposed at a filling port end of a valve stem portion 53, the vial coupling portion being accessible through an aperture 32 of the filling port 14.

The vial coupling portion 52 of the valve stem 50 is configured to engage with a keyed member 34 of a vial adapter 20 or of an external container in order to operate rotation of the valve stem by rotating the external container 16 or the vial adapter 20.

The valve mechanism 18 is operable to selectively open and close a first fluid path 54 and a second fluid path 56 such that only one of the fluid paths can be open at a time. Specifically, the first fluid path 54 is used for filling and the second fluid path 56 is used for drug delivery. The first fluid path 54 extends from the filling port 14 to the internal reservoir 8, whereby in a preferred embodiment the first fluid path 54 extends from the filling port 14 to the internal reservoir 8 via the pump 10. The second fluid path 56 extends from the internal reservoir 8 to the subcutaneous delivery mechanism 6 via the pump 10. Whether the first fluid path 54 or the second fluid path 56 is open is determined by the rotational position of the valve stem 50 in relation to the valve housing 48.

The valve housing 48 is provided with a first fluid channel 58 in communication with the internal reservoir 8 and a second fluid channel 60 in communication with the subcutaneous delivery mechanism 6. The valve mechanism 18 enables fluid to flow from the vial to recharge the internal reservoir and from the internal reservoir to the subcutaneous delivery mechanism 6. Hence, the fluid can flow in two directions through the first fluid channel 58 depending on if it is being operated to either direct fluid into the internal reservoir 8 or deliver fluid from the internal reservoir 8 to the subcutaneous needle 22 or catheter.

According to an embodiment of the invention, the forward or reverse direction of rotation of the pump 10 is controlled by rotation of the valve stem 50 between a first position and a second position. According to an embodiment the position of the valve stem 50 may in turn depend on the presence and angular position of the vial adapter 20. As illustrated in FIGS. 3a and 1b, when the vial adapter 20 is locked to the fil ling port, a sensor (not shown) controls the pump 10 to operate in a reverse direction (i.e. reverse to normal operation during drug delivery). When the vial adaptor 20 is removed, as shown in FIGS. 3*b* and 1*c*, the pump 10 may operate in its drug delivery direction to deliver the liquid through the valve to the user through the needle, cannula or catheter. The position of the valve stem 50 may thus be used to govern the direction of rotation of the pump 10. Moreover, the pump 10 may be activated to turn in one of the directions and also trigger a needle inserter device to insert a needle into the skin of the user.

Alternatively, according to another embodiment, the reverse direction of the pump 10 may be operated from the user interface in conjunction with a control unit of the drug delivery device 1.

Figure 4B:
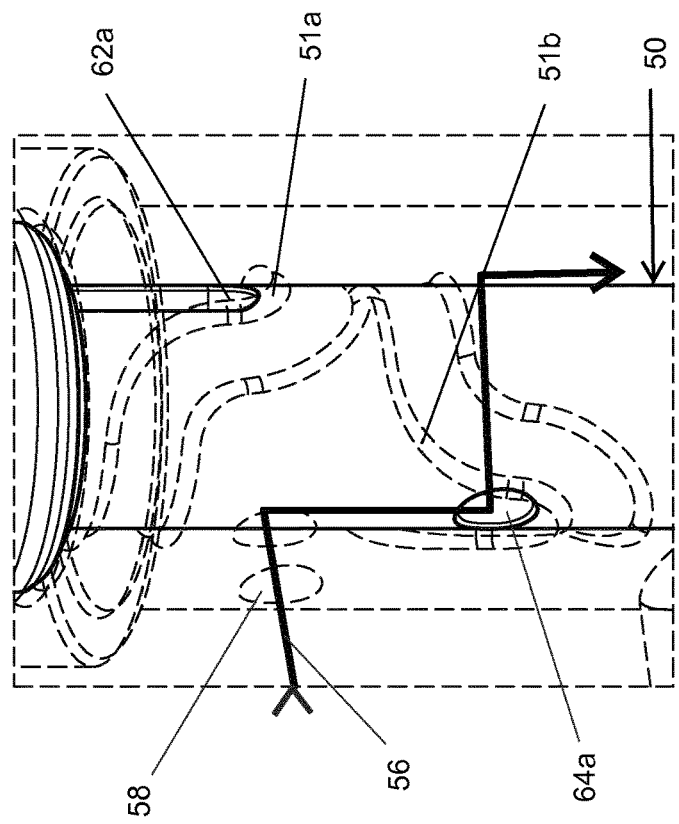
FIGS. 4a and 4b are perspective detail views of a portion of a valve mechanism of a drug delivery device according to an embodiment of the invention, FIG. 4a showing the valve mechanism in a first position for filling of the internal reservoir, and FIG. 4b showing the valve mechanism in a second position for drug delivery.
Figure 4A:
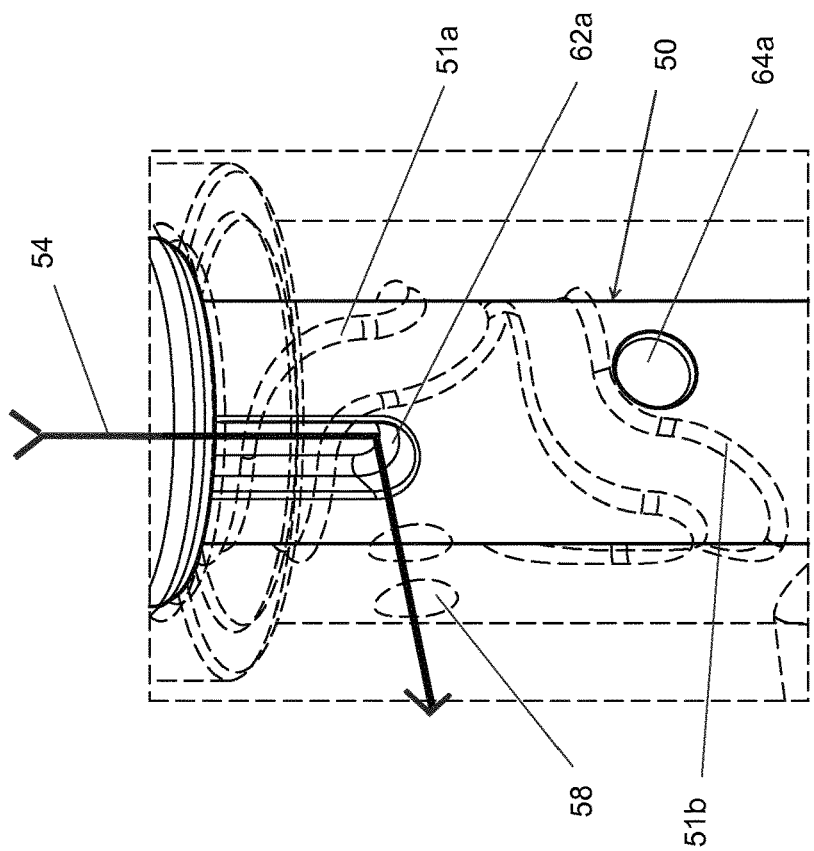

The valve housing 48 comprises a cavity 47 in which the valve stem 50 is received. The cavity comprises a sealing portion 51 in which the valve stem portion 53 is lodged, the sealing portion 51 comprising a ring seal 51*c* and first and second angular seals 51*a*, 51*b*. The ring seal 51*c* provides a hermetic seal between filling port 14 and first fluid channel 58 such that liquid flow between the filling port 14 and first fluid channel 58 can only pass through a first valve stem channel 62 formed in the valve stem 50. The first angular seal 51*a* is positioned between the filling port 14 and the first fluid channel 58, but closer, in an axial direction of the valve housing 48 to the filling port than the second fluid channel 60. The second angular seal 51*b* is positioned between the first fluid channel 58 and the second fluid channel 60. In order to selectively operate (i.e. open and close) the first fluid path 54 respectively the second fluid path 56, the valve stem 50 is provided with a first valve stem channel 62 and a second valve stem channel 64, whereby:

the first valve stem channel 62 is configured to bridge across the first angular seal 51*a* at a first rotational position of the valve stem, as best seen in FIGS. 3*a* and 4*a*, to establish a fluid connection between the vial adapter 20 and the internal reservoir 8; and the second valve stem channel 64 is configured to bridge across the second angular seal 51*b* at a second rotational position of the valve stem, as best seen in FIGS. 3*b* and 4*b*, to establish a fluid connection between the internal reservoir 8 and the subcutaneous delivery mechanism 6.

When the first angular seal 51*a* is bridged by the first valve stem channel 62, fluid communication between the filling port 14 and the first fluid channel 58 is established. When the second angular seal 51*b* is bridged by the second valve stem channel 64, fluid communication between the first fluid channel 58 and second fluid channel 60 is established.

The first fluid channel 62 comprises a first radial opening 62*a* on a circumferential surface of the valve stem 50, and the second fluid channel 64 comprises a second radial opening 64*a* on the circumferential surface of the valve stem 50*a*. In an embodiment the openings 62*a*, 64*a* are axially and angularly spaced apart from each other along the stem portion 53 of the valve stem 50. In a preferred embodiment, the openings 62*a*, 64*a* are separated by around 90° to 180° angular spacing around the circumference of the valve stem 50 and are at a separate axial positions in relation to the axial direction A of the valve stem 50 (whereby the axial direction is parallel to the axis of rotation of the valve stem). Rotation of the valve stem 50 between the first and second positions thus moves the first radial opening 62*a* from one side of the first angular seal 51*a* to the other side of said first angular seal 51*a* and simultaneously moves the second radial opening 64*a* from one side of the second angular seal 51*b* to the other side of said second angular seal 51*b* such that either the first angular seal 51*a* is bridged fluidically while the second angular seal 51*b* is not bridged (first position), or the second angular seal is bridged fluidically while the first angular seal is not bridged (second position).

The first and second angular positions of the valve stem 50 relative to the valve housing 48 may be defined by a stop 55*a* provided on the valve housing 48 configured to engage a complementary stop 55*b* provided on the valve stem 50 in the first and second angular positions. The stop 55*a* on the valve housing 48 and the stop 55*b* provided on the valve stem 50 are configured to guide the valve stem between the first position and the second position.

Rotation of the valve stem 50 may be effected by an external key member engaging in a keyed engaging slot 52*a* in the vial coupling portion 52 of the valve stem 50. Alternatively, in another embodiment, rotation of the valve stem 50 may be effected by a motor (not shown) controlled by the control unit of the drug delivery device 1, the control unit connected to a sensor detecting the presence of a vial fluidically coupled to the filling port 14 such that the valve stem 50 may only be rotated to the first position creating a fluid path between the filling port 14 and the internal reservoir 8 when the external vial 16 is coupled to the drug delivery device 1.

As best seen in FIGS. 3*a*, 5, and 8*a*-8*d*, the vial adapter 20 comprises a first connecting portion 24 and a second connecting portion 26. The first connecting portion 24 is configured such that the vial adapter 20 can be fixedly connected to the filling port 14 of the drug delivery device 1, and the second connecting portion 26 is configured such that the vial adapter 20 can be fixedly connected to a vial 16. The vial adapter 20 is provided with a channel 28 which extends between the first connecting portion 24 and the second connecting portion 26 in order to transfer fluid from the vial 16 into the valve mechanism 18 through the filling port 14. In an embodiment, the first connecting portion 24 comprises an extension 30 configured to be inserted into the filling port 14 and couple to the coupling portion 52 of the valve stem 50. Preferably, an annular seal 38 is provided on the extension 30 or an internal circumference of the valve housing 48 such that the extension is sealed against the internal circumference of the valve housing 48.

Preferably, for the first connecting portion 24 of the vial adapter 20, the vial adapter 20 and the filling port 14 are configured with mating male-female connecting members, such that the vial adapter 20 can be locked to the filling port 14 upon an axial insertion followed by a relative rotation, or by a spiral movement of simultaneous axial and rotational displacement, for instance where the mating connecting members form a bayonet coupling or a threaded connection.

In an embodiment, the filling port 14 located in the housing 7 of the delivery unit 2 comprises a keyed aperture 32 configured to receive axially therethrough a keyed member 34 of the vial adapter 20, Preferably, the keyed member 34 may be provided with two or more radial protrusions 36 extending transversely from the axial direction A of the channel 28. On the one hand the keyed member prevents axial removal of the vial adapter from the housing 7 once rotated from the second position to the first (locked) position.

Figure 8B:
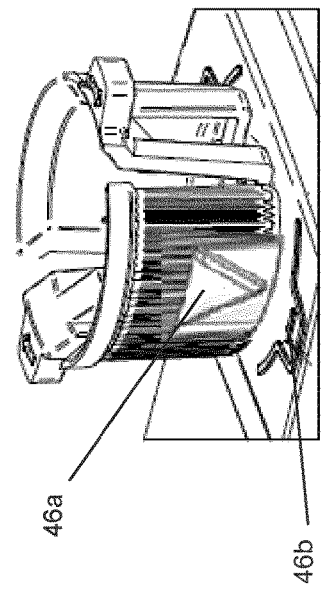
FIGS. 8a to 8c are perspective and cross-sectional views of a vial adapter of the mechanism of FIG. 5.
Figure 8D:
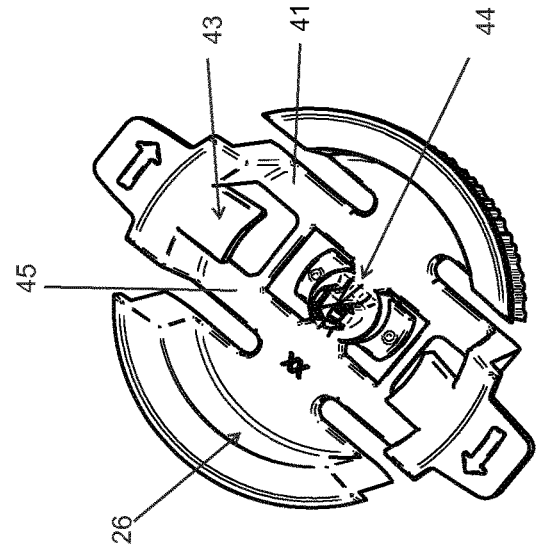
FIG. 8d is a perspective view of a vial adapter of the mechanism of FIG. 5 shown coupled to a filling port of the drug delivery device.
Figure 8A:
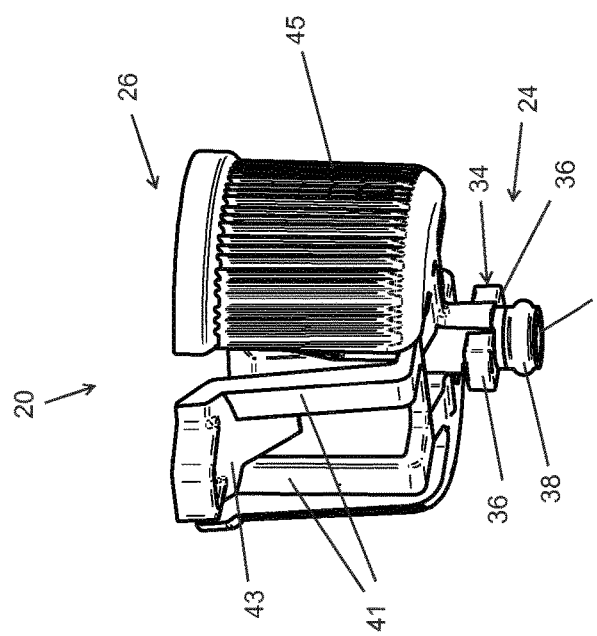
Figure 8C:
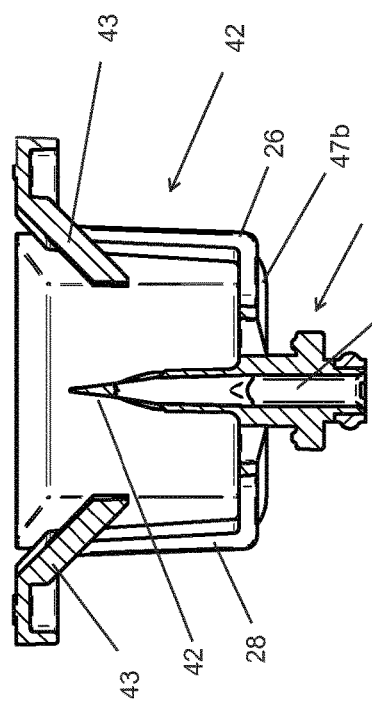

The second connecting portion 26, which is configured to connect the vial adapter 20 to the vial 16, may be provided with an internal thread (not illustrated) or a locking arm 40, in order to lock to a bottleneck of a vial 16 through a snap or a twist connection. The locking arm 40 may be connected to the vial adapter crown portion 45 via elastic support arms 41 as best seen in FIGS. 8a and 8b, to perform the snap connection as the vial rim 19 and neck 17 are inserted into the crown portion 45.

In an embodiment, the second connecting portion 26 is provided with a piercing member 42 adapted to penetrate a membrane, cover or septum 21 of a vial 16. The piercing member 42 may optionally have a venting channel or groove 44 to allow air to enter the vial to avoid an under-pressure in the vial 16, as liquid is being extracted therefrom.

The vial adapter 20 may advantageously be formed as a single integral part, for instance an injection molded polymer part.

Advantageously, the vial adapter 20 may also be provided with a position indicator 46a which aligns with a corresponding position indicator 46b on the housing 7 of the delivery unit 2 of the drug delivery device 1 when the vial adapter is in the first (locked) position. When the position indicator 46a of the vial adapter 20 is aligned with the position indicator 46b on the housing 7 of the delivery unit 2, the valve mechanism 18 is open such that a filling operation can be initiated.

In an embodiment, in order to lock the vial adapter 20 to the valve mechanism 18 and to open the first fluid path 54, the first connecting portion 24 of the vial adapter 20 is inserted into the filling port 14 and is thereafter rotated in relation to the housing 7 of the delivery unit 2 until the stops 55a, 55b abut defining the first position, whereby the user can check this by reference to the markers 46a. 46b. Friction bumps 47a, 47b provided on the housing 7 and vial adapter 20 (see FIGS. 1a and 8c) engage in the locked position to provide a stable locked position and to provide haptic feedback to the user when rotation from the second to the first (locked) position is completed and successful. Optionally, the vial adapter 20 may be provided with a corrugated surface or other grip-friendly surface on an outer side of the crown portion to improve grip for manual rotation of the vial adapter.

The drug delivery device may optionally be provided with a fill level detection window. Additionally or alternatively, a fill level detection can be provided by a digital message, such as a sound, vibration or a visual message on a display of the drug delivery device. The drug delivery device 1 can thus be configured such that a message is sent when it is time to refill and that a message is sent when the internal reservoir 8 is completely refilled. Additionally, the drug delivery device 1 may comprise a function to save date/time when last refill was done and check before distributing liquid that the time is not exceeding a predetermined value where the medicament is expired.

LIST OF FEATURES ILLUSTRATED

Drug delivery device 1
Base unit 4
  power source
  pump drive
  electronic control unit
    control unit user interface 5
Delivery unit 2
  Housing 7
    adhesive base 3
    position indicator 46b
    friction bumps 47a
  Internal reservoir 8
  Pump 10
    drive coupling interface 11
  Subcutaneous delivery mechanism 6
    Delivery needle 22
  liquid filling mechanism 12
    first fluid path 54
    second fluid path 56
    filling port 14
      keyed aperture 32
    valve mechanism 18
      Valve housing 48
        First fluid channel 58
        Second fluid channel 60
        Sealing portion 51
        First angular seal 51a
        Second angular seal 51b
        ring seal 51c
        Stop 55a
      Valve stem 50
        vial coupling portion 52
        52a keyed engaging slot
        stop 55b
        valve stem portion 53
        First valve stem channel 62
        first radial opening 62a
        Second valve stem channel 64
        second radial opening 64a
  Vial adapter 20
    First connecting portion 24
      annular seal 38
      keyed member 34
        radial protrusions 36
      Position indicator 46a
    Second connecting portion 26
      Piercing member 42
      Fluid channel 28
        Venting groove 44
      Locking arm 43
        elastic support arm 41
      crown portion 45
  External reservoir/Vial 16
    neck 17
    rim 19
    cover/septum 21

The invention claimed is:

1. A drug delivery device comprising a delivery unit including an internal reservoir, a subcutaneous delivery mechanism, a pump for pumping liquid from the internal reservoir to the subcutaneous delivery mechanism, and a liquid filling mechanism configured for injecting liquid from an external reservoir or vial into the internal reservoir, the liquid filling mechanism comprising a filling port and a valve mechanism selectively operable to:

open a first fluid path extending from the filling port to the internal fluid reservoir and close a second fluid path extending from the internal reservoir to the subcutaneous delivery mechanism, or close the first fluid path and open the second fluid path, wherein the valve mechanism comprises a valve housing fixedly mounted and rigidly coupled in relation to a housing of the drug delivery device and a valve stem received within the valve housing and arranged to rotate about an axial direction of the filling port, whereby the first fluid path and the second fluid path are selectively operated by the rotational position of the valve stem in relation to the valve housing, such that when the valve stem is in a first position, the first fluid path is open while the second fluid path is closed, and when the valve stem is in a second position, the second fluid path is open while the first fluid path is closed.

2. The drug delivery device according to claim 1, wherein the valve housing comprises a cavity comprising a sealing portion in which a valve stem portion of the valve stem is lodged, the valve stem portion comprising a first valve stem channel and a second valve stem channel, the valve housing comprising a first fluid channel fluidically connected to the internal reservoir and a second fluid channel fluidically connected to the subcutaneous delivery mechanism, the sealing portion further comprising a first angular seal positioned between the filling port and the first fluid channel, but before the second fluid channel, and a second angular seal positioned between the first fluid channel and the second fluid channel, whereby when the first angular seal is bridged by said first valve stem channel, fluid communication between the filling port and the first fluid channel is established, and when the second angular seal is bridged by said second valve stem channel, fluid communication between the first fluid channel and second fluid channel is established.

3. The drug delivery device according to claim 1, wherein the drug delivery device comprises a reusable base unit and a disposable delivery unit, and wherein the delivery unit houses the pump and the liquid filling mechanism.

4. The drug delivery device according to claim 1, wherein the liquid filling mechanism comprises a vial adapter which is configured to interconnect a vial to the filling port of the drug delivery device, the vial adapter and liquid filling mechanism comprising mating male-female connecting members, such that the vial adapter can be locked to the filling port upon an axial insertion followed by a rotation in relation to the housing, or by a spiral movement of simultaneous axial and rotational displacement, whereby in the locked position the first fluid path is opened and the second fluid path is closed, and when the vial adapter is in an unlocked position or removed from the filling port, the second fluid path is opened and the first fluid path is closed.

5. The drug delivery device according to claim 4, wherein the filling port comprises a keyed aperture configured to receive axially therethrough a keyed member of the vial adapter, the keyed member comprising at least one flange engaging a complementary locking member of the keyed aperture to hold the vial adapter to the fluid delivery device.

6. The drug delivery device according to claim 5, wherein the keyed member comprises two or more radial protrusions extending transversely from the axial direction of the vial adapter.

7. The drug delivery device according to claim 4, wherein the valve stem comprises a coupling portion arranged at a top end of a valve stem portion, the coupling portion being accessible through the filling port and configured to engage with the complementary keyed member of the vial adapter for driving rotation of the valve stem between the first position and the second position.

8. The drug delivery device according to claim 7, wherein the coupling portion of the valve stem is configured as a female connector, configured to engage with a male keyed member provided on the vial adapter.

9. The drug delivery device according to claim 2, wherein the first fluid channel and the second fluid channel of the valve stem connect to a lateral surface of the valve stem and are spaced apart at an angular distance of between 90° and 180°.

10. The drug delivery device according to claim 1, wherein the same pump is used for pumping fluid to the subcutaneous delivery mechanism and for pumping fluid to the internal fluid reservoir.

11. The drug delivery device according to claim 10, wherein the rotational position of the valve stem governs the direction of rotation of the pump.

12. The drug delivery device according to claim 4, wherein the vial adapter further comprising a position indicator cooperating with a position indicator on the liquid filling mechanism for guiding the user to turn the vial adapter to a required angle in which the valve stem is in the second position.

13. The drug delivery device according to claim 4, wherein the vial adapter comprises a first connecting portion configured such that the vial adapter can be fixedly connected to the filling port, and a second connecting portion configured such that the vial adapter can be fixedly connected to an external vial, the vial adapter further comprising a channel which extends from the first connecting portion to the second connecting portion in order to transfer fluid from the vial into the valve mechanism, the first connecting portion comprising an extension configured to be inserted into the filling port and couple to a coupling portion of the valve stem, a seal being provided on the extension or an internal circumference of the valve housing such that the extension is sealed against the internal circumference of the valve housing.

14. The drug delivery device according to claim 13, wherein the second connecting portion is provided with a piercing member adapted to penetrate a septum, membrane or a cover of a vial.

15. The drug delivery device according to claim 14, wherein the second connecting portion comprises a snap fit locking arm configured to lock the vial adapter to a neck of the vial.

* * * * *